United States Patent [19]

Di Giorgio et al.

[11] Patent Number: Plant 7,164

[45] Date of Patent: Feb. 20, 1990

[54] CARNATION NAMED DIGITOS

[75] Inventors: Antonio Di Giorgio; Renato Di Giorgio, both of San Remo, Italy

[73] Assignee: Laboratoire de Physiologie Vegetale, La Londe-Les Maures, France

[21] Appl. No.: 294,520

[22] Filed: Dec. 21, 1988

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new standard carnation variety particularly distinguished by its Venetian Pink flowers of medium size, which are produced profusely at recurrent intervals during the Spring, Midseason and Fall flowering periods on long, strong stems of a plant having a height of about 114 cm. at eight months of age. The flowers are borne singly on erect, rigid stems averaging about 84 cm. in length (cut at the tenth node); the plant itself having a vigorous, upright growth habit with moderately abundant foilage, well branched and developed with at least four stems emitted near the ground.

1 Drawing Sheet

BACKGROUND OF THE NEW PLANT

This new carnation cultivar originated as a seedling of a hybrid developed by us in 1984 at our nursery at San Remo, Italy by crossing two varieties of standard carnations selected from our collection of breeding plants maintained at our San Remo nursery for breeding purposes. This particular seedling was selected for propagation because of its very nice light pink coloration, its very full blooms having many clear pink petals, its strong and vigorous growth habit, and its profuse production of blooms. Asexual propagation of this selected seedling was done by us and under our direction, at our San Remo nursery, with such satisfactory results that we directed propagation of this new plant be continued from generation to generation by cuttings of successive generations until we were satisfied that the novel characteristics of this new plant would be retained from generation to generation and so that its homogeneity would be assured.

This new standard carnation is now being propagated on a commercial scale by Establissements Barberet et Blanc, at Laboratoire de Physiologie Vegetale, 83250 La Londe-Les Maures, France.

DESCRIPTION OF THE DRAWING

This new carnation cultivar is illustrated by the accompanying photographic drawing, which shows several blooming stems including flowers at various stages of maturity with one of the stems showing a bud just prior to its bursting into a full flower, the color rendition shown being as nearly true to that herein specified as is reasonably possible to obtain by professional photographic procedures.

DESCRIPTION OF THE NEW PLANT

The following is a detailed description of our new standard carnation cultivar based upon observation of plants grown in greenhouse, as well as out of doors, at our nursery at San Remo, Italy, as well as at the nursery of Laboratoire de Physiologie Vegetale maintained at 83250 Le Londe-Les Maures, France, the color designations stated herein being according to The R.H.S. Colour Chart published by The Royal Holticultural Society of London, England.

THE PLANT

Origin: Seedling.

Parentage:

*Seed parent.*—Carnation variety No. 11 (unpatented).

*Pollen parent.*—Carnation variety No. 845 (unpatented).

Both varieties are identified in our breeding records maintained in our nursery offices at San Remo, Italy.

Classification:

*Botanic.*—*Dianthus caryophyllus.*

*Commercial.*—Standard Carnation.

Form: Erect bush having at least four stems emitted near the ground.

Height: Averaging about 114 cm. at eight months of growth.

Main stem:

*Length.*—Less than 15 cm. due to pinching.

Growth habit: Vigorous, upright and rigid.

Branching character: Average.

Foilage:

*Quantity.*—Moderately abundant.

*Number of leaves.*—More than 120.

*Leaf size.*—(At the seventh node). Averages about 14.2 cm. long and 1.2 cm. wide.

*Leaf shape.*—Oblong with rolled margins.

*Texture.*—Leathery.

*Ribs and veins.*—Hardly noticeable.

*Rachis.*—Not noticeable.

*Color.*—Both upper and lower sides, 189-A/B.

*Leaflets.*—None.

THE BUD

Size: Small.

*Diameter.*—Averages about 3 cm.

*Length.*—Averages about 2.7 cm.

Shape: Ovoid.

Rate of opening: Normal.

Color of Petals: When sepals first divide, Light Pink. When petals begin to unfurl, the same as the full bloom.

Sepals:

*Number.*—Five or six.

*Shape.*—Generally ovate but joined together at the lower parts and having an acuminate apex.

*Character.*—The sepals are hooded over the bud until parting and as the flower opens, the sepals curl back.

*Color.*—Inside, 145-D. Outside, 145-B and 143-C.

*Striae.*—Longitudinal.

Calyx:

*Shape.*—Bell-shaped.

*Size.*—Large.

*Splitting.*—A little splitting sometimes occurs.

*Aspect.*—Smooth.

Flower stem:

*Character.*—Erect and rigid.

*Length.*—Averages about 84 cm., cut at the tenth node.

THE FLOWER

Blooming habit: Recurrent, blooming profusely in the Spring, Midseason and Fall blooming periods with a tendency to give few blooms in the Fall.

Size of flower: Medium.

*Diameter.*—Averages about 8 cm.

*Depth.*—Averages about 5 cm.

Borne: Singly on long, strong, upright stems.

Shape: When bloom first opens, high-centered. When bloom matures, dome-shaped.

Petalage:

*Number of petals.*—Averaging about 136.

*Arrangement.*—Imbricated.

*Form.*—Fan-shaped with very rounded edges and a lightly serrated apex.

*Texture.*—Leathery.

*Appearance.*—Satiny.

*Color.*—Outer and inside petals: Body—Venetian Pink, 49-B/C. Base—Greenish White. Reverse side—49-C.

*Petaloids.*—Number: 9 to 19. Size: Smaller than the petals. Color: The same as the petals.

Flower stem:

*Character.*—Upright with good strength.

*Color.*—189-A/B.

Fragrance: Light.

Discoloration after full bloom: Very Little.

Persistence: On the plant, the flowers hang on and dry.

Lasting quality: As a cut flower, at least ten days in vase keeping.

THE REPRODUCTIVE ORGANS

Stamens:

*Number.*—10 to 13.

*Arrangement.*—Around the ovary.

*Anthers.*—Size: Less than 4 mm. Color: Whitish.

*Filaments.*—Length: Averages about 2.5 cm. Color: Whitish.

Pistils:

*Number.*—3 to 5.

*Styles.*—Length: Averages about 1.5 cm. Color: Whitish.

*Stigma.*—Color: Whitish.

Character of ovaries: Ribbed.

We claim:

1. The new and distinctive carnation plant, substantially as herein shown and described, particularly characterized by its light pink, medium sized flowers which are produced profusely on long, strong, upright stems having moderately abundant foilage.

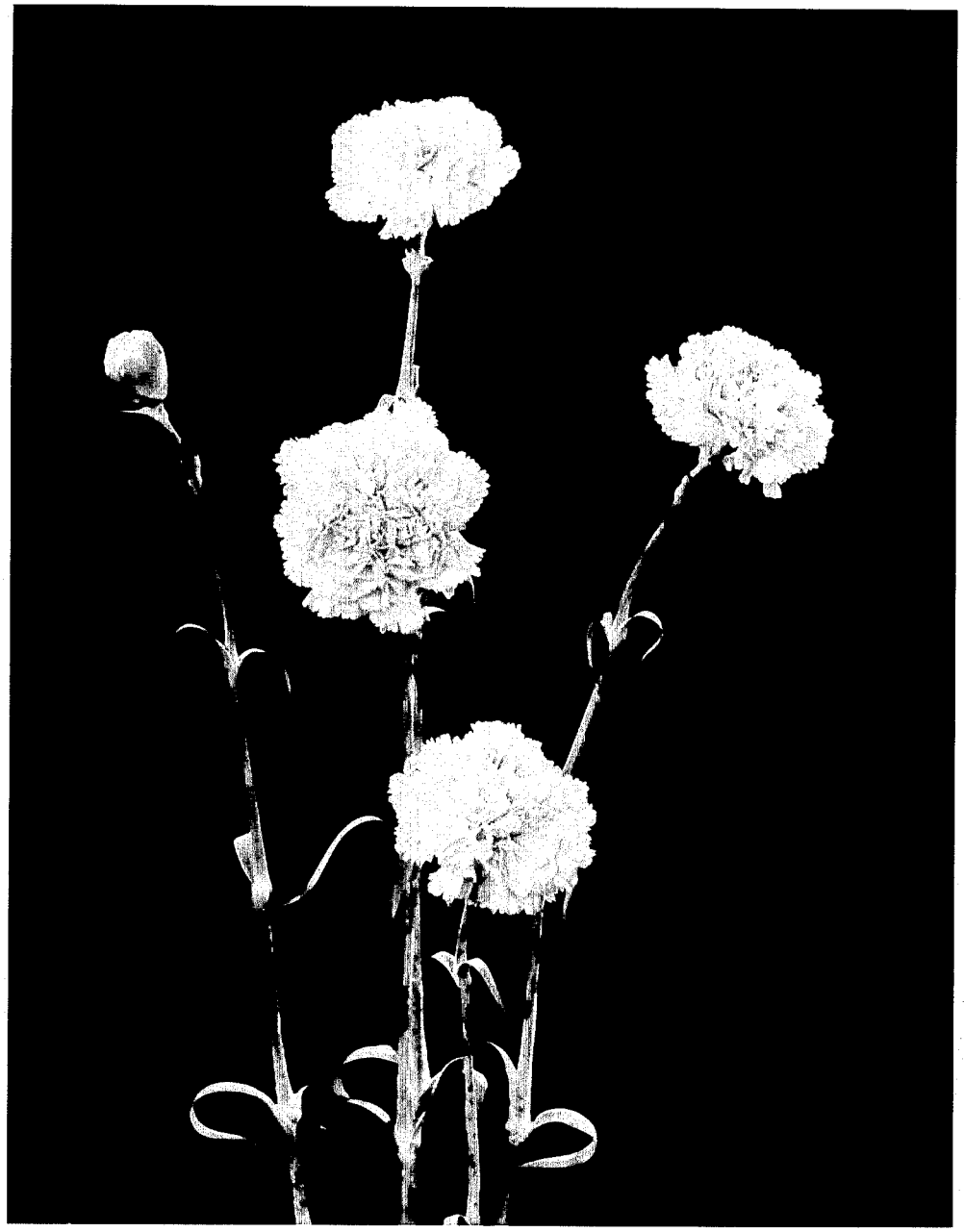

* * * * *